United States Patent [19]

Petusky

[11] Plant 4,252

[45] May 16, 1978

[54] CHRYSANTHEMUM PLANT NAMED TOPAZ

[75] Inventor: Kerry S. Petusky, West Chicago, Ill.

[73] Assignee: Pan-American Plant Company, West Chicago, Ill.

[21] Appl. No.: 795,308

[22] Filed: May 9, 1977

[51] Int. Cl.[2] ..... A01H 5/00

[52] U.S. Cl. ..... Plt./78

[58] Field of Search ..... Plt./78

*Primary Examiner*—Robert E. Bagwill

*Attorney, Agent, or Firm*—Chas. W. Rummler

[57] ABSTRACT

A new and distinct variety of chrysanthemum plant of the standard type for greenhouse culture for the production of cut flowers, characterized by its very large blooms which have a greyed orange to dark Naples yellow color when flowered under cool to moderate temperatures and a bright green-yellow color when flowered under high temperatures. This plant has a vigorous growth habit, excellent bench and cut flower life, and a high tolerance to high soluble salt conditions.

5 Drawing Figures

BACKGROUND OF THE NEW PLANT

My new chrysanthemum cultivar was discovered by me in August 1974 as a sport of an unidentified seedling growing among a group of greenhouse plants maintained at West Chicago, Ill., for use in breeding endeavors carried on with the object of developing improved chrysanthemum varieties for the commercial market. This flower caught my attention because of its very large size and good golden color and by means of cuttings from the flowering stem, I reproduced the plant and found the cultivar to have retained the same flower characteristics that I had seen on the original plant. Propagation of the new plant through successive generations, by vegetative cuttings, at West Chicago, Ill., has demonstrated that its novel characteristics hold true from generation to generation and appear to be firmly fixed.

Propagation of this new variety by vegetative cuttings is now being carried on at West Chicago, Ill., and at Cortez, Fla.

DESCRIPTION OF THE DRAWINGS

This new chrysanthemum plant is illustrated by the accompanying drawings, the first of which is a photographic print in full color showing blossoms of the plant flowered in December 1976, the colors shown being as nearly true as it is reasonably possible to obtain by conventional photographic procedures. The second sheet of the drawings is a print of a machine copy of typical leaves of the new plant showing their distinctive character.

DESCRIPTION OF THE NEW PLANT

The following is a detailed description of my new chrysanthemum cultivar with color designations according to the R.H.S. Colour Chart published by The Royal Horticultural Society of London, England.

THE PLANT

Origin: Sport.

Parentage: An unidentified seedling.

Classification:

*Botanic.*—*Chrysanthemum morifolium.*

*Commercial.*—Greenhouse cut flower.

Form: Upright bush.

Height: 3 to 4½ feet.

Growth: Vigorous, sturdy, and with very good strength.

Branching: Under natural conditions.

Foliage: Quantity — abundant with 6 to 8 leaves per 6 inches of stem.

*Leaf size.*—Length — 4½ to 6½ inches. Width — 2⅜ to 3½ inches.

*Leaf shape.*—Lobed lanceolate and slight serrated.

*Surface texture.*—Canescent.

*Venation.*—Pinnately.

*Color.*—Upper side — 147A. Under side — 147B.

*Petioles.*—⅜ to 1⅛ inches long.

THE BUD

Form: Globular.

Size: ½ to ⅝ inch in diameter and ¼ to ⅜ inch in depth.

Opening rate: Bud opens slowly.

Color:

*When phyllaries divide.*—144A and 144B.

*When florets begin to unfurl.*—162A and 176D.

Phyllaries: The outside of the receptacle bears many involucral bracts which stand up and are spear shaped.

*Color.*—Inside — 137A. Outside — 137B.

*Surface texture.*—Pubescent.

Peduncle: Erect and ½ to ⅞ inch long.

*Surface texture.*—Pubescent.

THE FLOWER

Recommended flowering: Year around with appropriate photoperiod control.

Response: 9 week.

Natural flowering season: About October 27 to November 4.

Flower type: Composite and incurved standard.

Blooms:

*Borne.*—Singly. A head of many florets carried on a receptacle.

*Size.*—Very large. Diameter: 5 to 6½ inches. Depth: 4 to 5½ inches.

*Shape.*—A somewhat flat ball when bloom first opens, becoming more globular as bloom matures.

*Florets.*—Numerous in number. Form: Incurved. Firmness: Medium. Appearance: Very light shine.

| Color: | Jan. | April | June | Aug. | Dec. |
|---|---|---|---|---|---|
| Outer florets: | | | | | |
| Top side - | 167C | 162A | 5A | 5A | 11A |
| Reverse - | 10B | 8B | 7D | 7D | 160A |
| Inner florets: | | | | | |
| Top side - | 22A | 163B | 7A | 6A | 11A |
| Reverse - | 8B | 162A | 9C | 8B | 160A |

Peduncle: Upright and sturdy.
*Length.*—½ to ⅞ inch.
*Color.*—146A.
Persistence: Florets hang on and dry.
Fragrance: Typical chrysanthemum.
Lasting Quality:
*On plant.*—4 to 5 weeks.
*As cut flower.*—13 to 23 days.

REPRODUCTIVE ORGANS

Stamens: Number — 5.
*Arrangement.*—Syngenesious.
*Filaments.*—1/16 to ⅛ inch long. Color: Light yellow
*Pollen.*—Color — Yellow.
Pistils: Number — One for each ray and disc floret.

*Styles.*—⅛ to 3/16 inch long.
*Stigmas.*—Color — Yellow.
Ovaries: Inferior bicarpellate in character.

This new cultivar of chrysanthemum is particularly characterized by its very large flower size and its natural range of color variation according to the time of flowering during the year. When flowered under cool to moderate temperatures, the ray florets are of a generally greyed orange or dark Naples yellow color and when flowered under high temperatures, the color is of a bright greenish yellow. Thus, as indicated by the flower color chart herein, the colors may range from a greyed orange in January to a greyed yellow for April flowering, then to a bright yellow when flowered in the summertime, and finally a dark Naples yellow in December.

Other distinctions of my new plant are its resistance to shatter and botrytis, its excellent bench and cut flower life, its uniform 9-week response the year around with very few culls, and its tolerance of high soluble salt conditions.

I claim:

1. A new chrysanthemum cultivar, substantially as herein shown and described, characterized by its very large flower size, its uniform 9-week year around response, and its tolerance to high soluble salt conditions.

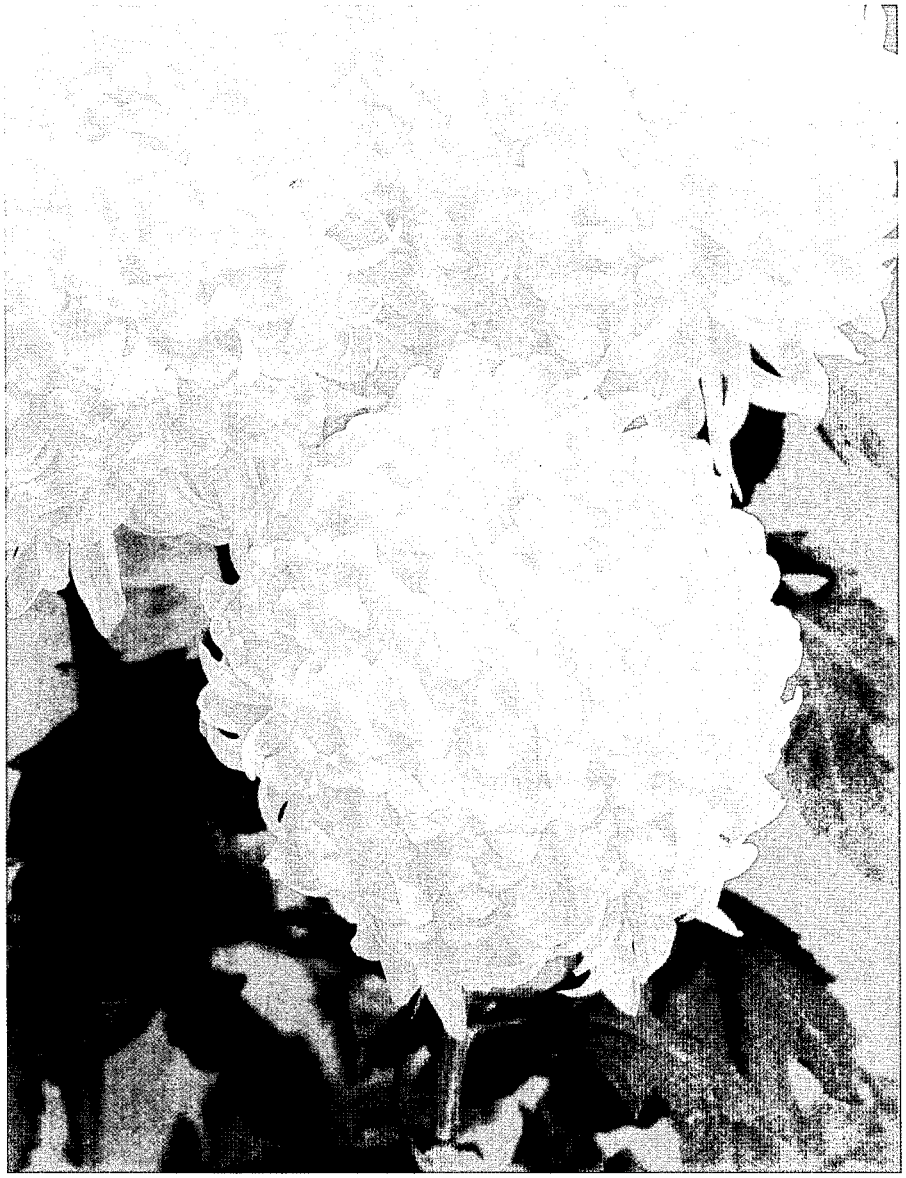

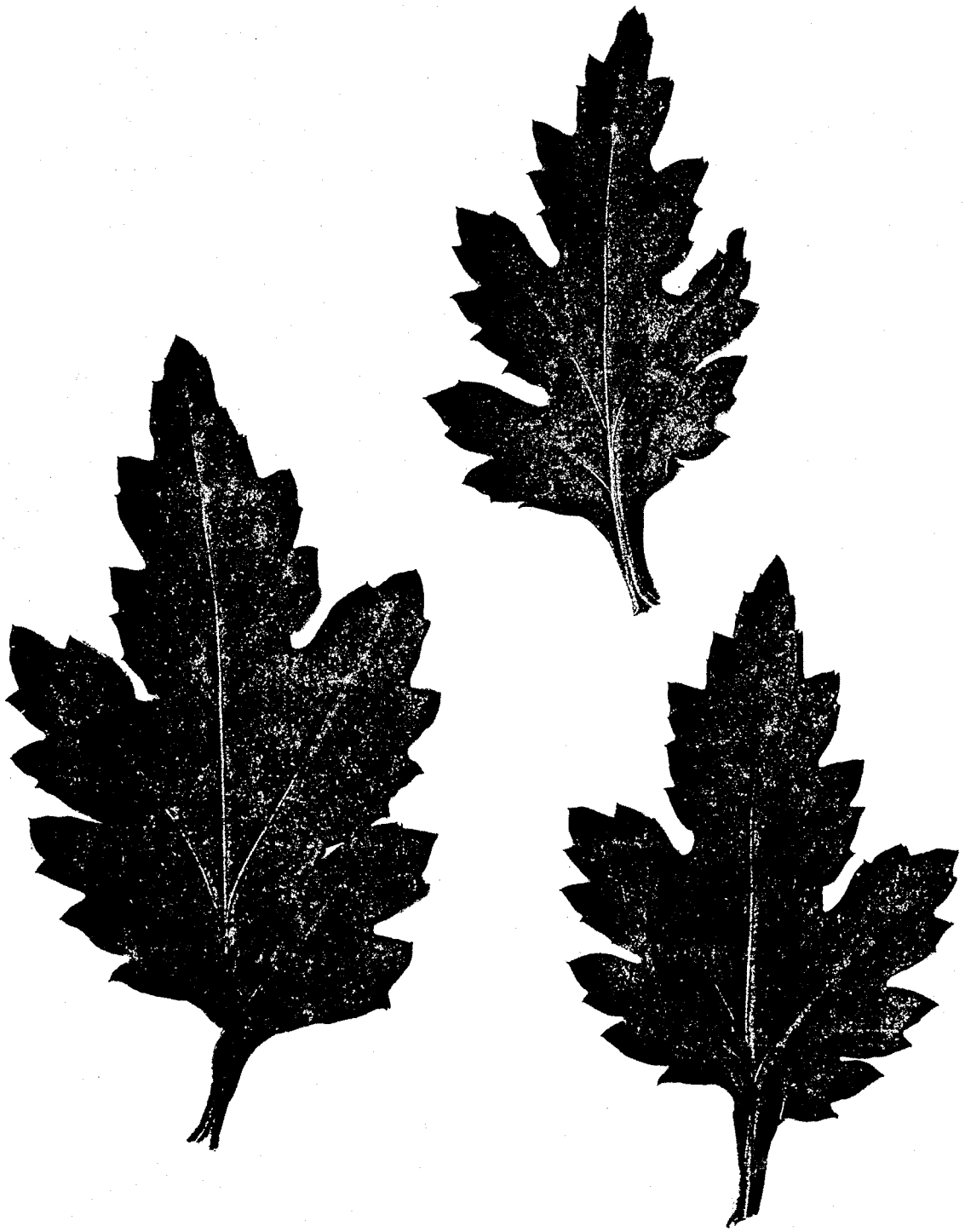

* * * * *